US009498187B2

United States Patent
Kim et al.

(10) Patent No.: US 9,498,187 B2
(45) Date of Patent: Nov. 22, 2016

(54) METHOD AND APPARATUS FOR DISPLAYING ULTRASOUND IMAGE

(71) Applicant: Samsung Medison Co., Ltd., Gangwon-do (KR)

(72) Inventors: Jeong-i Kim, Gangwon-do (KR); Sung-hee Kim, Gangwon-do (KR); Suk-jin Lee, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 13/676,862

(22) Filed: Nov. 14, 2012

(65) Prior Publication Data

US 2013/0131512 A1    May 23, 2013

(30) Foreign Application Priority Data

Nov. 22, 2011    (KR) .................. 10-2011-0122400

(51) Int. Cl.
  *A61B 8/00* (2006.01)
  *A61B 8/08* (2006.01)
  *A61B 8/13* (2006.01)
  *G06T 11/20* (2006.01)
  *G06F 19/00* (2011.01)

(52) U.S. Cl.
  CPC ............ *A61B 8/465* (2013.01); *A61B 8/13* (2013.01); *A61B 8/463* (2013.01); *A61B 8/5292* (2013.01); *G06F 19/321* (2013.01); *G06T 11/206* (2013.01)

(58) Field of Classification Search
  CPC .. A61B 8/463; A61B 8/5238; A61B 8/0825; A61B 8/13; A61B 8/4281; A61B 8/465; A61B 8/5292; G06F 19/321; G06F 19/3406; G06F 19/3437; G06T 11/206

USPC .................... 600/437–469; 382/128–132
  See application file for complete search history.

(56) References Cited

U.S. PATENT DOCUMENTS

| | | | |
|---|---|---|---|
| 6,370,413 B1 * | 4/2002 | Alvarez et al. ............... | 600/407 |
| 6,458,081 B1 | 10/2002 | Matsui et al. | |
| 6,511,430 B1 | 1/2003 | Sherar et al. | |
| 6,859,288 B1 | 2/2005 | Brackett et al. | |
| 7,044,912 B2 * | 5/2006 | Babu et al. ................... | 600/437 |
| 7,615,008 B2 * | 11/2009 | Zhang et al. ................. | 600/437 |

(Continued)

FOREIGN PATENT DOCUMENTS

| | | | |
|---|---|---|---|
| JP | 2005-301567 A | 10/2005 | |
| JP | 2006-141508 A | 6/2006 | |

(Continued)

OTHER PUBLICATIONS

Korean Office Action with English translation issued in Korean Application No. 10-2011-0122400 mailed Jun. 25, 2013.

(Continued)

*Primary Examiner* — Sanjay Cattungal
(74) *Attorney, Agent, or Firm* — McDermott Will & Emery LLP (57) ABSTRACT

A method of displaying an ultrasound image, the method including acquiring patient identification information; providing an examination list including a bookmark used to identify at least one ultrasound image based on the acquired patient identification information; receiving selection information regarding the at least one ultrasound image included in the examination list; and displaying the ultrasound image selected based on the selection information.

9 Claims, 4 Drawing Sheets

(56) References Cited

U.S. PATENT DOCUMENTS

| | | | |
|---|---|---|---|
| 7,727,151 B2* | 6/2010 | Zhang et al. | 600/443 |
| 7,828,733 B2* | 11/2010 | Zhang et al. | 600/437 |
| 8,043,216 B2* | 10/2011 | Matsumura | 600/438 |
| 8,162,833 B2* | 4/2012 | Zhang et al. | 600/437 |
| 8,216,143 B2* | 7/2012 | Gunji | 600/440 |
| 8,496,586 B2* | 7/2013 | Zhang et al. | 600/437 |
| 8,538,103 B2* | 9/2013 | Chono | 382/128 |
| 2004/0066398 A1* | 4/2004 | Dolimier et al. | 345/720 |
| 2005/0049500 A1* | 3/2005 | Babu et al. | 600/443 |
| 2005/0054921 A1* | 3/2005 | Katsman et al. | 600/437 |
| 2005/0171430 A1* | 8/2005 | Zhang et al. | 600/437 |
| 2006/0247527 A1* | 11/2006 | Maruyama | 600/443 |
| 2007/0038085 A1* | 2/2007 | Zhang et al. | 600/437 |
| 2008/0269606 A1* | 10/2008 | Matsumura | 600/438 |
| 2009/0171209 A1* | 7/2009 | Kim et al. | 600/443 |
| 2010/0036248 A1* | 2/2010 | Chouno | 600/443 |
| 2010/0040274 A1* | 2/2010 | Zhang et al. | 382/131 |
| 2010/0280375 A1* | 11/2010 | Zhang et al. | 600/443 |
| 2011/0077520 A1* | 3/2011 | Osawa | 600/443 |
| 2011/0098566 A1* | 4/2011 | Zhang et al. | 600/443 |
| 2011/0313291 A1* | 12/2011 | Chono | 600/440 |
| 2012/0016238 A1* | 1/2012 | Matsumura | 600/438 |
| 2012/0027276 A1* | 2/2012 | Chono | 382/128 |
| 2012/0116218 A1* | 5/2012 | Martin et al. | 600/437 |
| 2013/0202169 A1* | 8/2013 | Lee et al. | 382/131 |
| 2013/0251633 A1 | 9/2013 | Borden et al. | |

FOREIGN PATENT DOCUMENTS

| | | |
|---|---|---|
| JP | 2007-144175 A | 6/2007 |
| JP | 4071710 | 1/2008 |
| JP | 2009-106505 A | 5/2009 |
| KR | 2009-0070412 A | 7/2009 |
| WO | WO-03/001421 A1 | 1/2003 |

OTHER PUBLICATIONS

Korean Notice of Allowance with English translation issued in Korean Application No. 10-2011-0122400 mailed Aug. 28, 2013.

Office Action issued Dec. 5, 2012 in Korean Patent Application No. 10-2011-0122400.

Extended European Search Report issued in European Application No. 12161003.4 dated Jan. 22, 2014, 7 pgs.

* cited by examiner

FIG. 5

METHOD AND APPARATUS FOR DISPLAYING ULTRASOUND IMAGE

CROSS-REFERENCE TO RELATED PATENT APPLICATION

This application claims the benefit of Korean Patent Application No. 10-2011-0122400, filed on Nov. 22, 2011, in the Korean Intellectual Property Office, the disclosure of which is incorporated herein in its entirety by reference.

BACKGROUND OF THE INVENTION

1. Field of the Invention

The present invention relates to a method and apparatus for displaying an ultrasound image to provide examination lists including bookmarks and an ultrasound image corresponding to an examination item selected by a user.

2. Description of the Related Art

Ultrasound diagnosis apparatuses transmit an ultrasound signal toward a predetermined part of the body from a body surface of an object and obtain a tomogram of soft-tissues or an image of blood flow by using information regarding the ultrasound signal reflected by tissues of the body.

Ultrasound diagnosis apparatuses have various advantages, including a compact size, low cost, and real-time display. Also, ultrasound diagnosis apparatuses have excellent stability because there is no fear of X-ray exposure, and thus, the ultrasound diagnosis apparatuses are widely used together with various other diagnosis apparatuses, such as computerized tomography scanners, magnetic resonance imaging (MRI) apparatuses, nuclear medicine diagnosis apparatuses, or the like.

In general, ultrasound diagnosis apparatuses do not provide a function of searching for an ultrasound image. That is, when a user searches for an ultrasound image of a previously diagnosed patient, the user needs to search for the ultrasound image by checking diagnosis dates and thumbnail images one by one. Thus, it takes much time to search for the ultrasound image desired by the user.

Furthermore, current ultrasound diagnosis apparatuses do not search for a plurality of ultrasound images having common characteristics simultaneously, and do not provide users with comparison data of the plurality of ultrasound images. That is, if a patient undergoes various examinations during a predetermined period of time like determining growth progress of an embryo or a prognosis of a lesion, current ultrasound diagnosis apparatuses need to inconveniently search for and compare and analyze images having a specific lesion or clinical significance from all stored image lists.

SUMMARY OF THE INVENTION

The present invention provides a method and apparatus for displaying an ultrasound image, which provide a user with a function of bookmarking an ultrasound image so that the user can easily search for the bookmarked ultrasound image.

According to an aspect of the present invention, there is provided a method of displaying an ultrasound image, the method including: acquiring patient identification information; providing an examination list including a bookmark used to identify at least one ultrasound image based on the acquired patient identification information; receiving selection information regarding the at least one ultrasound image included in the examination list; and displaying the ultrasound image selected based on the selection information.

The providing of the examination list may include: providing the examination list including the bookmark in a bar chart. In this case, the method may include: analyzing an amount of ultrasound images of at least one examination item included in the examination list; setting a length of a bar corresponding to the at least one examination item based on the analyzed amount of ultrasound images; and providing the examination list including the bookmark in the bar chart according to the set length of the bar.

The method may include receiving bookmark selection information to select at least one bookmark included in the examination list; and selecting at least one bookmark based on the bookmark selection information and displaying the ultrasound image corresponding to the selected at least one bookmark.

The method may include: receiving a plurality of pieces of ultrasound image selection information to select a plurality of ultrasound images included in the examination list; and selecting the plurality of ultrasound images based on the plurality of pieces of ultrasound image selection information and displaying measurement values corresponding to the selected plurality of ultrasound images in a graph chart. In this regard, the method may include: determining whether a same measurement item is included in the selected plurality of ultrasound images; if it is determined that the same measurement item is included in the selected plurality of ultrasound images, generating comparison data between the measurement values corresponding to the selected plurality of ultrasound images; and displaying the generated comparison data in the graph chart.

The method may include: receiving ultrasound image diagnosis department selection information to select at least one ultrasound image diagnosis department;

and selecting the at least one ultrasound image diagnosis department based on the ultrasound image diagnosis department selection information, and providing the examination list corresponding to the selected at least one ultrasound image diagnosis department.

According to another aspect of the present invention, there is provided an apparatus for displaying an ultrasound image, the apparatus including: a receiving unit for acquiring patient identification information, and receiving selection information regarding at least one ultrasound image included in an examination list; a display unit for providing the examination list including a bookmark used to identify the at least one ultrasound image based on the acquired patient identification information, and displaying the ultrasound image selected based on the selection information; and a control unit for controlling the receiving unit and the display unit.

According to another aspect of the present invention, there is provided a computer readable recording medium storing a program for executing a method of displaying an ultrasound image.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

First, the terms used in the present disclosure will be briefly described below before exemplary embodiments of the present invention are described in greater detail.

Most of the terms used herein are general terms that have been widely used in the technical art to which the present invention pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present invention.

In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the terms, such as 'unit' or 'module', etc., should be understood as a unit that processes at least one function or operation and that may be embodied in a hardware manner, a software manner, or a combination of the hardware manner and the software manner.

Throughout the specification, the term 'ultrasound image' means an image of a target, which is captured using ultrasound waves. Here, the 'target' may be understood to be part of a human body. For example, the target may be an organ of a human body, such as the liver, the heart, the womb, a brain, the breast, or the abdomen, or a fetus.

The ultrasound image may be embodied in any of various forms. For example, the ultrasound image may include at least one selected from the group consisting of a brightness (B) mode image, a color (C) mode image, and a Doppler (D) mode image. According to an embodiment of the present invention, the ultrasound image may be a two-dimensional (2D) or three-dimensional (3D) image.

Throughout the specification, the term 'user' may be a medical professional, e.g., a doctor, a nurse, a clinical pathologist, or a medical imaging professional, but is not limited thereto.

The present invention will now be described more fully with reference to the accompanying drawings, in which exemplary embodiments of the invention are shown. This invention may, however, be embodied in many different forms and should not be construed as being limited to the embodiments set forth herein. Rather, these embodiments are provided so that this disclosure will be thorough and complete and will fully convey the concept of the invention to those of ordinary skill in the art. For clarity, in the drawings, constitutional elements that are not related to embodiments of the present invention are not illustrated. The same reference numerals represent the same elements throughout the drawings. As used herein, the term "and/or" includes any and all combinations of one or more of the associated listed items. Expressions such as "at least one of," when preceding a list of elements, modify the entire list of elements and do not modify the individual elements of the list.

Figure 1:
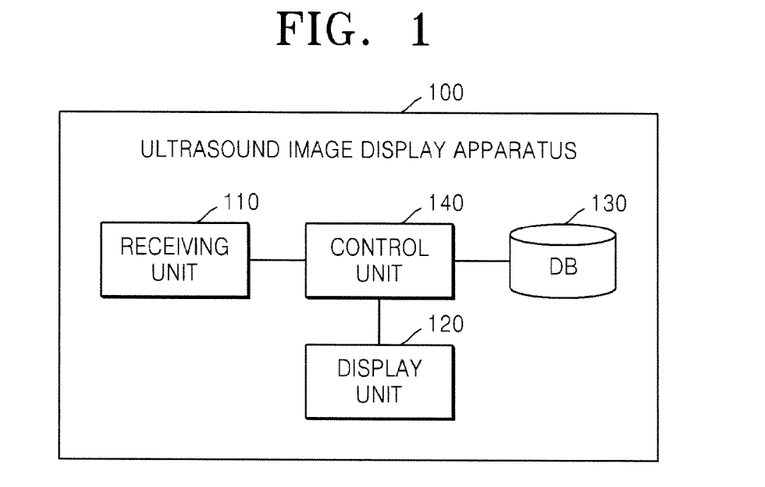
FIG. 1 is a block diagram of an ultrasound image display apparatus according to an embodiment of the present invention.

FIG. 1 is a block diagram of an ultrasound image display apparatus 100 according to an embodiment of the present invention.

Referring to FIG. 1, the ultrasound image display apparatus 100 of the present embodiment is a device for acquiring an ultrasound image, storing the ultrasound image, and displaying the ultrasound image to a user. The ultrasound image display apparatus 100 may acquire an ultrasound image acquired by itself or receive an ultrasound image from the outside.

The ultrasound image display apparatus 100 according to the present embodiment may be implemented in various ways. For example, the ultrasound image display apparatus 100 described in the present specification may include an ultrasound diagnosis apparatus, a general purpose computer system, a laptop, a personal digital assistant (PDA), a tablet PC, and the like.

Meanwhile, the ultrasound image display apparatus 100 according to the present embodiment may provide the user with a bookmarking function. Bookmarking is an indication used to identify at least one ultrasound image. For example, if there is a region assumed to be a disease or an image having a measured clinical significance during a review of an ultrasound image, the user may bookmark the ultrasound image.

According to an embodiment of the present invention, as shown in FIG. 1, the ultrasound image display apparatus 100 may include a receiving unit 110, a display unit 120, a storage unit 130, and a control unit 140. However, the elements of FIG. 1 are not indispensable elements. The ultrasound image display apparatus 100 may include a greater number of elements or a lesser number of elements.

The receiving unit 110 may acquire patient identification information. The patient identification information according to the present embodiment is information used to identify a patient, such as an ID of the patient, an ID number, a name, a birth date, and the like. According to an embodiment of the present invention, if the user selects specific patient identification information, the receiving unit i110 acquires the patient identification information selected by the user.

The receiving unit 110 may receive ultrasound image selection information included in examination lists. In this case, the receiving unit 110 may receive a plurality of pieces of ultrasound image selection information included in the examination lists. That is, the user may select a specific ultrasound image from the examination lists corresponding to the patient identification information, and select two or more ultrasound images.

According to an embodiment of the present invention, the receiving unit 110 may receive bookmark selection information. The bookmark selection information according to the present embodiment is a user's selection information regarding a bookmark indicated in an ultrasound image. According to an embodiment of the present invention, the receiving unit 110 may receive a plurality of pieces of bookmark selection information.

Therefore, according to an embodiment of the present invention, the user may select a specific bookmark from a displayed screen, and review a corresponding ultrasound image, thereby reducing a user's ultrasound image search time.

Meanwhile, the receiving unit 110 may receive ultrasound image diagnosis department selection information. The ultrasound image diagnosis department selection information is selection information regarding a diagnosis department that diagnoses an ultrasound image. For example, an ultrasound image diagnosis department may include an OB (Obstetrics) department, a GYN (Gynecology) department, a PD (Pediatrics) department, a CS (Chestsurgery) department, a RD (Radiology) department, a NS (Neurosurgery) department, and the like.

The display unit 120 may output information processed by the ultrasound image display apparatus 100. The display unit 120 may provide examination lists including bookmarks corresponding to the acquired patient identification information.

In this regard, according to an embodiment of the present invention, the examination lists may include thumbnails of time-sequentially arranged ultrasound images.

According to another embodiment, the display unit 120 may provide the examination lists in a bar chart. The examination lists according to the present embodiment may include a plurality of examination items EXAM. The examination items EXAM are past examination details of a specific patient divided by a predetermined unit.

For example, ultrasound images 1, 2, and 3 captured on May 1, 2011 may be configured as one examination item (for example, EXAM 1), and ultrasound images a, b, c, d, and e captured on Jul. 1, 2011 may be configured as another examination item (for example, EXAM 2).

According to an embodiment of the present invention, the display unit 120 may display the examination lists by differentiating lengths of bars based on an amount of ultrasound images of the plurality of examination items EXAM. Meanwhile, according to an embodiment of the present invention, the display unit 120 may display a bookmarked ultrasound image based on the bookmark selection information. The display unit 120 may also display measurement values included in a plurality of ultrasound images in a graph chart. The graph chart may include a bar graph, a curve line graph, a circle graph, a radial graph, a histogram, and the like but the present invention is not limited thereto.

According to an embodiment of the present invention, if the user selects the ultrasound image diagnosis department, the display unit 120 may provide an examination list including a bookmark corresponding to the selected ultrasound image diagnosis department.

Meanwhile, if the display unit 120 and a touch pad form a mutual layer structure and thus are configured as a touch screen, the display unit 120 may be used as an input device other than an output device. The display unit 120 may include at least one of a liquid crystal display (LCD), a thin film transistor-liquid crystal display (TFT-LCD), an organic light-emitting diode (OLED), a flexible display, and a 3D display. The ultrasound image display apparatus 100 may include two or more display units 120 according to how the ultrasound image display apparatus 100 is implemented.

The storage unit 130 may store patient information, an ultrasound image, diagnosis data, etc. The patient information of the present embodiment may include information regarding patient personal identification information (an ID, an ID number, a name, a birth date, and the like), a medical history, a singularity, and the like. The diagnosis data may include measured result information, content analyzed by the user, a user's opinion on abnormality, a singularity, and the like regarding the ultrasound image.

According to an embodiment of the present invention, the storage unit 130 may be embedded in the ultrasound image display apparatus 100 or may be an external memory. The storage unit 130 also may be a storage server implemented on the Web.

The storage unit 130 of the present embodiment may classify and store ultrasound image data, according to patients and diagnosis dates. For example, the storage unit 130 may store ultrasound images in a unit of the examination items EXAM. Thus, the examination item EXAM of the present embodiment may include a plurality of ultrasound images.

Meanwhile, according to another embodiment of the present invention, the storage unit 130 may store ultrasound images per diagnosis departments. The storage unit 130 may also store bookmark information indicated by the user.

The control unit 140 may generally control the receiving unit 110, the display unit 120, and the storage unit 130. For example, the control unit 140 may analyze the amount of ultrasound images of the plurality of examination items included in the examination lists, and set lengths of bars corresponding to the plurality of examination items based on the analyzed amount of ultrasound images.

The control unit 140 may determine whether the same measurement item is included in a plurality of ultrasound images selected by the user, and, if the same measured item is included therein, may generate comparison data between measurement values included in the plurality of ultrasound images selected by the user A method of displaying an ultrasound image to a user by using each element of the ultrasound image display apparatus 100 will now be in detail described with reference to FIGS. 2 through 5.

Figure 2:
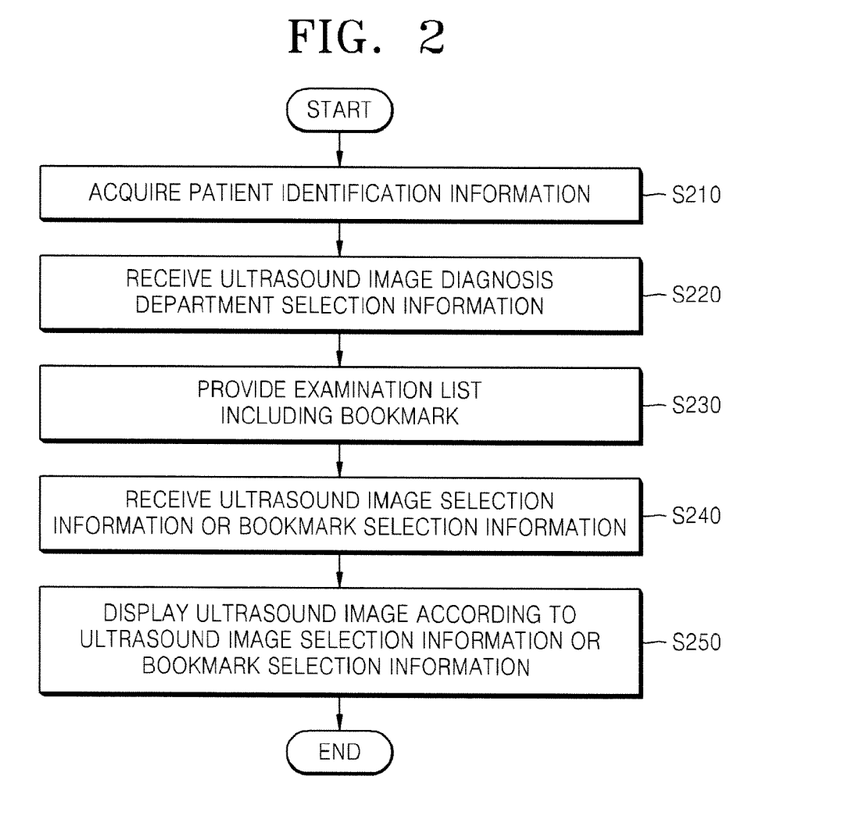
FIG. 2 is a flowchart illustrating a method of displaying an ultrasound image, according to an embodiment of the present invention.

FIG. 2 is a flowchart illustrating a method of displaying an ultrasound image, according to an embodiment of the present invention.

Referring to FIG. 2, according to the present embodiment, the ultrasound image display apparatus 100 may acquire patient identification information (operation S210). For example, if a user wants to review an ultrasound image of a patient A and inputs an ID of the patient A, the ultrasound image display apparatus 100 acquires patient identification information of the patient A.

Meanwhile, according to an embodiment of the present invention, when the user selects a patient ID from a work list, the ultrasound image display apparatus 100 may acquire the patient identification information.

According to an embodiment of the present invention, the ultrasound image display apparatus 100 may receive ultrasound image diagnosis department selection information (operation S220). That is, the user may select the patient identification information on the work list and a clinic department in which an ultrasound image is analyzed. For example, if the user wants to review an ultrasound image regarding the patient A analyzed in an OB/GYN department, the user may input the patient identification information of the patient A, and select OB/GYN from among clinic departments.

The ultrasound image display apparatus 100 may provide an examination list including a bookmark corresponding to the acquired patient identification information (operation S230). According to an embodiment of the present invention, the examination list may be provided in a thumbnail format. According to another embodiment of the present invention, the examination list may be provided in a bar chart. This will be described in detail with reference to FIG. 3.

According to an embodiment of the present invention, the ultrasound image display apparatus 100 may display examination lists in an order of diagnosis times. The ultrasound image display apparatus 100 may also display examination lists including a plurality of examination items EXAM in an ascending order of an amount of ultrasound images or in an ascending order of bookmarks.

Meanwhile, if the ultrasound image diagnosis department selection information is received, the ultrasound image display apparatus 100 may provide an examination list including a bookmark corresponding to a selected diagnosis department. That is, if ultrasound images of patients are diagnosed in a plurality of clinic departments through a comprehensive medical check, the ultrasound image display apparatus 100 may display an ultrasound image diagnosed in a selected diagnosis department.

According to an embodiment of the present invention, the ultrasound image display apparatus 100 may receive ultrasound image selection information included in the examination lists (operation S240). In this case, the ultrasound image display apparatus 100 may receive one ultrasound image selection information or a plurality of pieces of ultrasound image selection information. For example, the user may select an ultrasound image A included in the examination lists or the ultrasound image A and an ultrasound image B.

In this regard, the user may select a plurality of ultrasound images in the same examination item EXAM or extract a plurality of ultrasound images in different examination items EXAM.

According to an embodiment of the present invention, the ultrasound image display apparatus 100 may receive bookmark selection information. In this case, the user may select one bookmark or a plurality of bookmarks.

According an embodiment of the present invention, the ultrasound image display apparatus 100 may display ultrasound images according to the ultrasound image selection information or the bookmark selection information (operation S250). For example, according to an embodiment of the present invention, if the user selects an ultrasound image included in an examination list, the ultrasound image display apparatus 100 may display the selected ultrasound image.

According to another embodiment of the present invention, if the user selects a bookmark, the ultrasound image display apparatus 100 may display a bookmarked ultrasound image according to the bookmark selection information.

Figure 3:
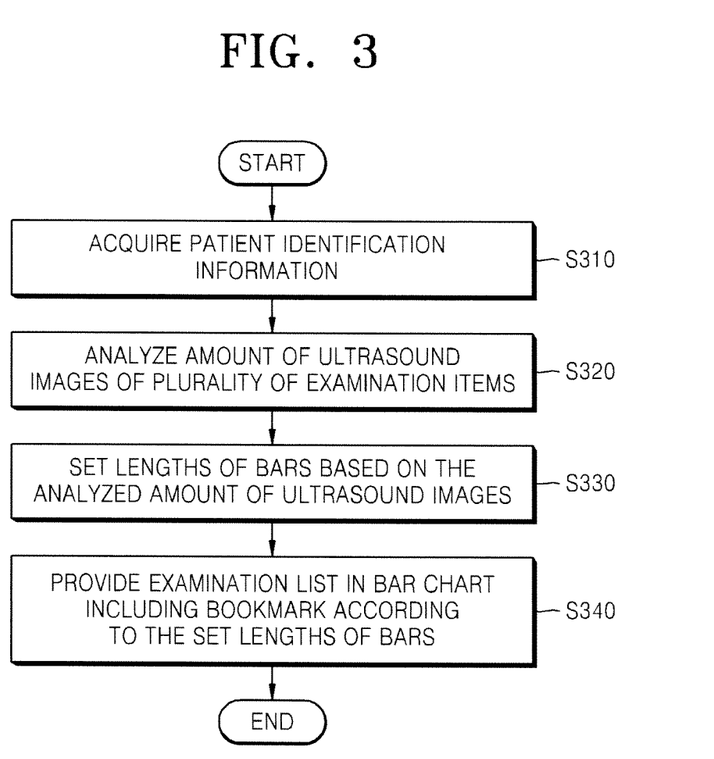
FIG. 3 is a flowchart illustrating a method of providing an examination list in a bar chart, according to an embodiment of the present invention.

FIG. 3 is a flowchart illustrating a method of providing an examination list in a bar chart, according to an embodiment of the present invention.

Referring to FIG. 3, according to the present embodiment, the ultrasound image display apparatus 100 may acquire patient identification information (operation S310). In this case, the ultrasound image display apparatus 100 may analyze an amount of ultrasound images of a plurality of examination items included in the examination list corresponding to the acquired patient identification information (operation S320).

The ultrasound image display apparatus 100 may set lengths of bars corresponding to the plurality of examination items based on the analyzed amount of ultrasound images (operation S330). For example, if three ultrasound images are included in an examination item 1 EXAM 1, and nine ultrasound images are included in an examination item 2 EXAM 2, lengths of bars corresponding to the examination item 2 EXAM 2 may be set three times longer than those corresponding to the examination item 1 EXAM 1.

The ultrasound image display apparatus 100 may provide the examination list in the bar chart including a bookmark according to the set lengths of the bars. Thus, according to an embodiment of the present invention, a user may intuitively check the amount of ultrasound images included in each examination item EXAM.

Figure 4:
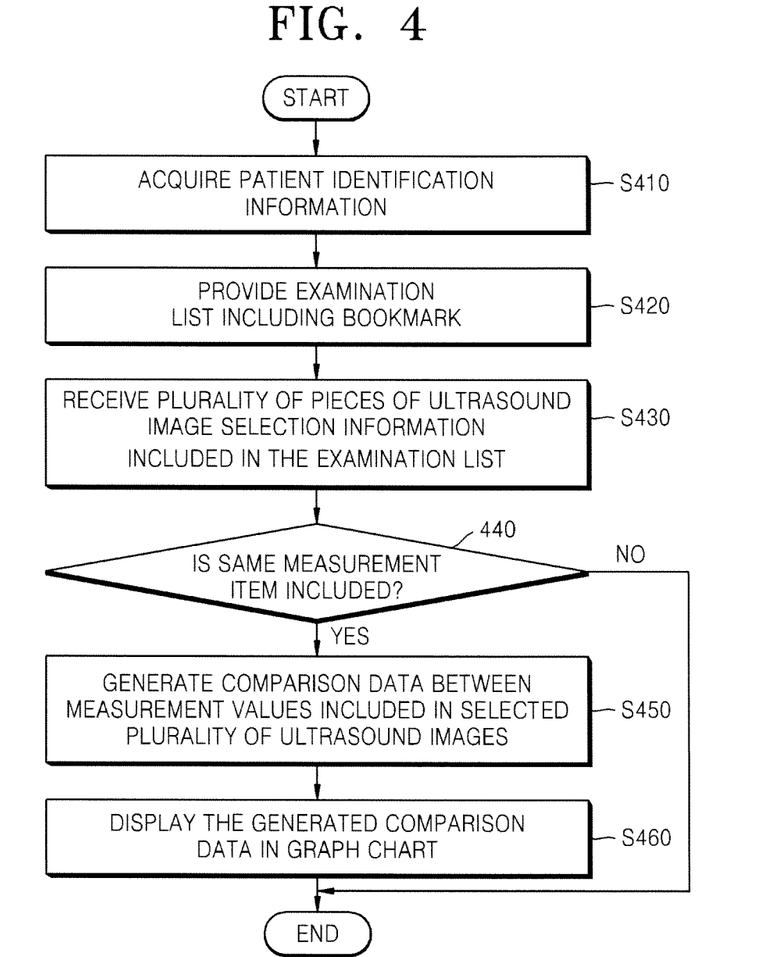
FIG. 4 is a flowchart illustrating a method of displaying comparison data between measurement values included in a plurality of ultrasound images in a graph chart, according to an embodiment of the present invention.

FIG. 4 is a flowchart illustrating a method of displaying comparison data between measurement values included in a plurality of ultrasound images in a graph chart, according to an embodiment of the present invention.

Referring to FIG. 4, according to the present invention, the ultrasound image display apparatus 100 may acquire patient identification information (operation S410).

The ultrasound image display apparatus 100 may provide an examination list including a bookmark corresponding to the acquired patient identification information (operation S420).

In this case, the ultrasound image display apparatus 100 may receive a plurality of pieces of ultrasound image selection information included in the examination list (operation S430). According to an embodiment of the present invention, the ultrasound image display apparatus 100 may receive a plurality of pieces of bookmark selection information.

The ultrasound image display apparatus 100 according to an embodiment of the present invention may determine whether the same measurement item is included in selected plurality of ultrasound images (operation S440). Measurement items according to the present embodiment may include at least one of a BPD (bi-parietal diameter), an OFD (occipitofrontal diameter), and an AC (abdominal circumference), but the present invention is not limited thereto.

If the same measurement item is included in a selected plurality of ultrasound images, the ultrasound image display apparatus 100 may generate the comparison data between the measurement values included in the selected ultrasound images (operation S450). For example, if the BPD item is included in ultrasound images A, B, and C selected by a user, the ultrasound image display apparatus 100 may compare BPD values included in the ultrasound images A, B, and C.

The ultrasound image display apparatus 100 may display the generated comparison data in the graph chart (operation S460). Thus, according to an embodiment of the present invention, it is useful in comparing a plurality of examination items EXAM like a growth progress of an embryo or a prognosis of a lesion.

Meanwhile, the graph chart according to the present embodiment may be applied in various ways as occasion demands.

Figure 5:
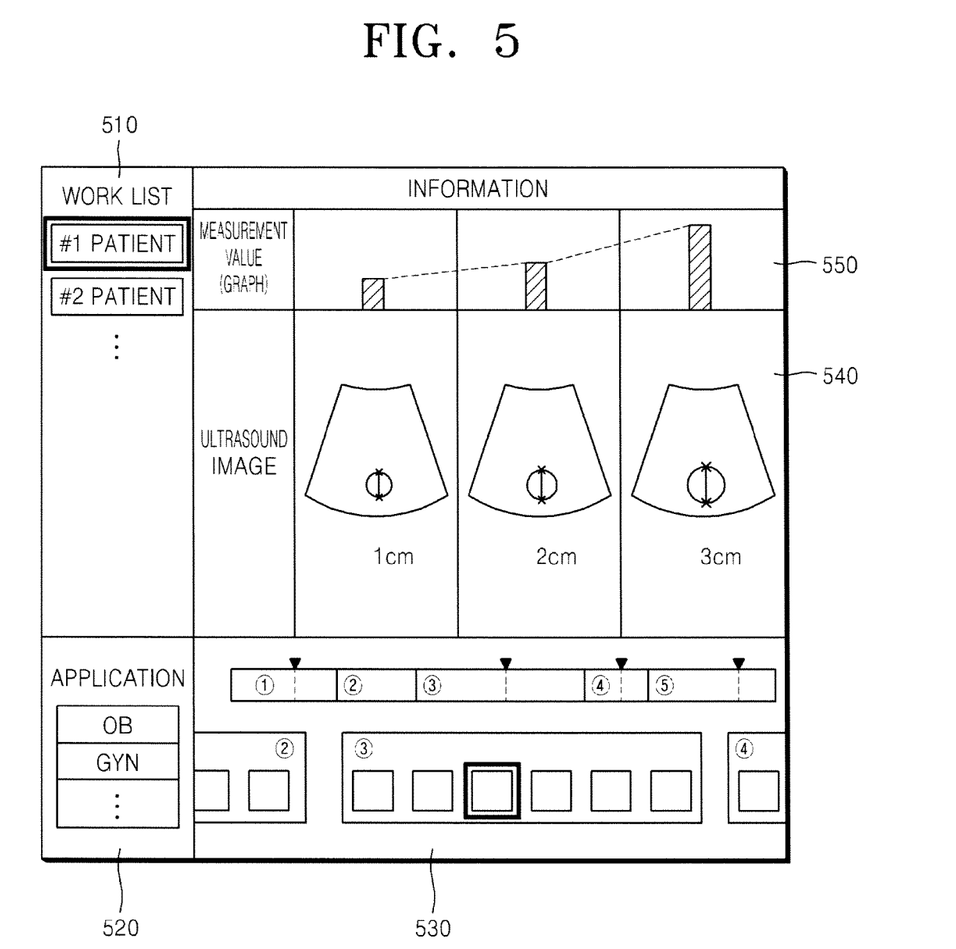
FIG. 5 is a diagram of an example of a screen displaying an ultrasound image, according to an embodiment of the present invention.

FIG. 5 is a diagram of an example of a screen displaying an ultrasound image, according to an embodiment of the present invention. Referring to FIG. 5, patient identification information may be displayed on a work list 510. A user may select identification information (for example, an ID) of a patient of which an ultrasound image is to be checked from the work list 510.

The user may also select a diagnosis department 520 if the user is to search for an ultrasound image diagnosed in a predetermined diagnosis department. For example, if the user wishes to see a growth progress of an embryo, the user may select an OB department.

If the user inputs the patient identification information and/or diagnosis department selection information, the ultrasound image display apparatus 100 may display a corresponding examination list 530. In this case, the ultrasound image display apparatus 100 may display the examination list 530 including bookmark information (for example, ▼).

Meanwhile, the ultrasound image display apparatus 100 may adjust lengths of bars in the examination list 530 based on an amount of ultrasound images of a plurality of examination items EXAM. For example, as shown in FIG. 5, since an examination item ☐ (EXAM ☐) includes six ultrasound images, which is the most, the ultrasound image display apparatus 100 may adjust a bar corresponding to the examination item ☐ (EXAM ☐) to be the longest.

If the user selects an ultrasound image or a bookmark, the ultrasound image display apparatus 100 may display ultrasound images 540 based on a user's selection. If the same measurement item is included in a selected plurality of ultrasound images, the ultrasound image display apparatus 100 may provide comparison data of measurement values in a graph chart 550.

For example, as shown in FIG. 5, the ultrasound image display apparatus 100 may display BPD values included in ultrasound images 1, 2, and 3 in a bar graph chart. In this case, the user may visually see a growth progress of an embryo.

Embodiments of the present invention include a computer-readable recording medium including program commands for executing operations implemented through various computers. The computer-readable recording medium can store program commands, data files, data structures, or combinations thereof. The program commands recorded in the computer-readable recording medium may be specially designed and configured for the present invention or be known to those of ordinary skill in the field of computer software. Examples of a computer-readable recording medium include magnetic media such as hard disks, floppy disks, and magnetic tapes, optical media such as CD-ROMs and DVDs, magneto-optical media such as floptical disks, or hardware devices such as ROMs, RAMs, and flash memories, which are specially configured to store and execute program commands. Examples of the program commands include a machine language code created by a compiler and a high-level language code executable by a computer using an interpreter and the like. The computers may include the control unit 140 of the ultrasound image display apparatus 100.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of displaying an ultrasound image, the method comprising:
   acquiring patient identification information;
   displaying, on a first area of an ultrasound image display, an examination list including a plurality of bookmark images used to respectively identify a plurality of ultrasound images bookmarked by a user based on the acquired patient identification information;
   receiving selection information regarding bookmark images selected from among the plurality of bookmark images included in the examination list;
   displaying, on a second area of the ultrasound image display which is different from the first area, ultrasound images corresponding to the selected bookmark images, the displayed ultrasound images including ultrasound images, which correspond to the patient identification information, obtained on different days;
   generating comparison data between measurement values corresponding to the displayed ultrasound images; and
   displaying the generated comparison data in a graph chart on a third area of the ultrasound image display.

2. The method of claim 1, wherein the providing of the examination list comprises:
   providing the examination list including the plurality of bookmark images in a bar chart.

3. The method of claim 2, wherein the providing of the examination list including the plurality of bookmark images in the bar chart comprises:
   analyzing an amount of ultrasound images of at least one examination item included in the examination list;
   setting a length of a bar corresponding to the at least one examination item based on the analyzed amount of ultrasound images; and
   providing the examination list including the plurality of bookmark images in the bar chart according to the set length of the bar.

4. The method of claim 1, wherein the providing of the examination list including the plurality of bookmark images further comprises:
   receiving ultrasound image diagnosis department selection information to select at least one ultrasound image diagnosis department; and
   selecting the at least one ultrasound image diagnosis department based on the ultrasound image diagnosis department selection information, and providing the examination list corresponding to the selected at least one ultrasound image diagnosis department.

5. A non-transitory computer readable medium storing a program therein, for execution by a processor, for the method of displaying an ultrasound image of claim 1.

6. An apparatus for displaying an ultrasound image, the apparatus comprising:
   a receiving unit for acquiring patient identification information, and receiving selection information regarding bookmark images selected from among a plurality of bookmark images included in an examination list;
   a display unit for providing, on a first area of the display unit, the examination list including the bookmark images used to respectively identify a plurality of ultrasound images bookmarked by a user based on the acquired patient identification information, and displaying, on a second area of the display unit which is different from the first area, the ultrasound images corresponding to the selected bookmark images, the displayed ultrasound images including ultrasound images, which correspond to the patient identification information obtained on different days; and
   a control unit for, generating comparison data between measurement values corresponding to the displayed ultrasound images; and displaying the generated comparison data in a graph chart on a third area of the display unit.

7. The apparatus of claim 6, wherein the display unit provides the examination list including the plurality of bookmark images in a bar chart.

8. The apparatus of claim 7, wherein the control unit analyzes an amount of ultrasound images of at least one examination item included in the examination list, and sets a length of a bar corresponding to the at least one examination item based on the analyzed amount of ultrasound images,
   wherein the display unit provides the examination list including the plurality of bookmark images in the bar chart according to the set length of the bar.

9. The apparatus of claim 6, wherein the receiving unit receives ultrasound image diagnosis department selection information to select at least one ultrasound image diagnosis department,
  wherein the control unit selects the at least one ultrasound image diagnosis department based on the ultrasound image diagnosis department selection information, and provides the examination list corresponding to the selected at least one ultrasound image diagnosis department.

* * * * *